(12) United States Patent
Han et al.

(10) Patent No.: US 6,230,548 B1
(45) Date of Patent: May 15, 2001

(54) SYSTEM FOR TESTING PROPERTIES OF MATERIALS

(76) Inventors: Chi-Neng Arthur Han, 3711 Hamilton St., Philadelphia, PA (US) 19104; Robert K. Yang, 138-10 Franklin Ave., Apt. 2C, Flushing, NY (US) 11355; Alex J. Phinn, 112 Taylor St., Bristol, PA (US) 19007

( * ) Notice: Subject to any disclaimer, the term of this patent is extended or adjusted under 35 U.S.C. 154(b) by 0 days.

(21) Appl. No.: 09/115,042

(22) Filed: Jul. 14, 1998

(Under 37 CFR 1.47)

(51) Int. Cl.[7] .................................................. G01N 33/00
(52) U.S. Cl. ................................................. 73/38; 73/866
(58) Field of Search .............................. 73/866, 104, 38, 73/150 R, 159

(56) References Cited

U.S. PATENT DOCUMENTS

| | | |
|---|---|---|
| 2,353,852 | 7/1944 | Rowland et al. . |
| 2,667,070 * | 1/1954 | Sockman et al. ...................... 73/104 |
| 2,868,062 | 1/1959 | Haley . |
| 3,559,475 | 2/1971 | Dillon et al. . |
| 3,731,529 | 5/1973 | Pepmeier et al. . |
| 3,830,094 * | 8/1974 | Leger ...................................... 73/104 |
| 4,259,862 | 4/1981 | Sheaks et al. . |
| 4,541,273 | 9/1985 | Bery . |
| 4,803,872 | 2/1989 | Crawford et al. . |
| 4,911,003 * | 3/1990 | Bares ...................................... 73/159 |
| 4,976,138 | 12/1990 | Benninghoff et al. . |
| 5,065,620 | 11/1991 | Bares . |
| 5,141,767 | 8/1992 | Peterson et al. . |
| 5,325,713 | 7/1994 | Furst et al. . |
| 5,438,864 * | 8/1995 | Morgan ................................... 73/149 |
| 5,503,005 * | 4/1996 | Carlton ................................... 73/866 |

* cited by examiner

*Primary Examiner*—Robert Raevis
(74) *Attorney, Agent, or Firm*—Klehr, Harrison, Harvey, Branzburg & Ellers; John F. Letchford

(57) ABSTRACT

A system including methods and apparatus for measuring properties of a material, such as surface tension, surface energy, absorption, adsorption, permeability, porosity and printability and the like. A chemical marker containing test liquid is applied to the material and excess test liquid not retained by the material is removed. Thereafter, either the removed test liquid or the test liquid retained by the material is analyzed to determine the amount of chemical marker substance in the test liquid and, thus, the desired property of the material.

22 Claims, 4 Drawing Sheets

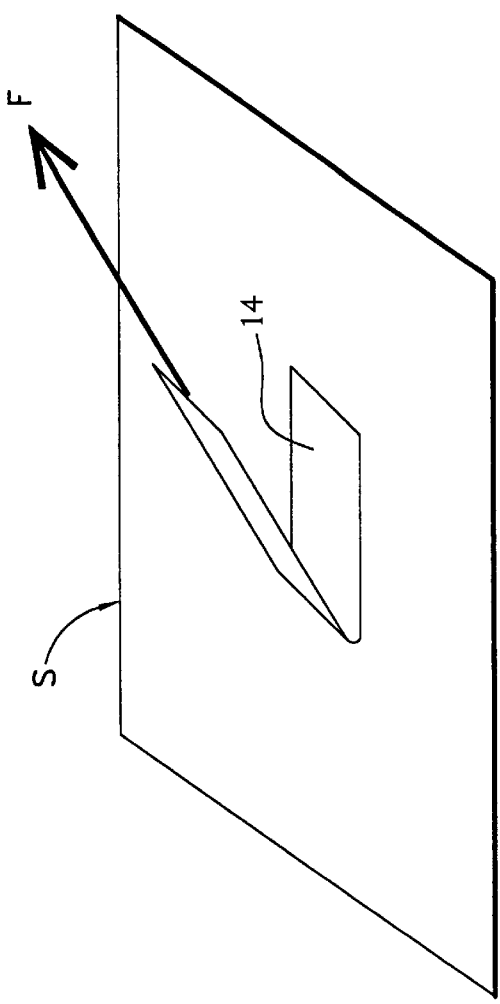
FIG. 1
FIG. 2
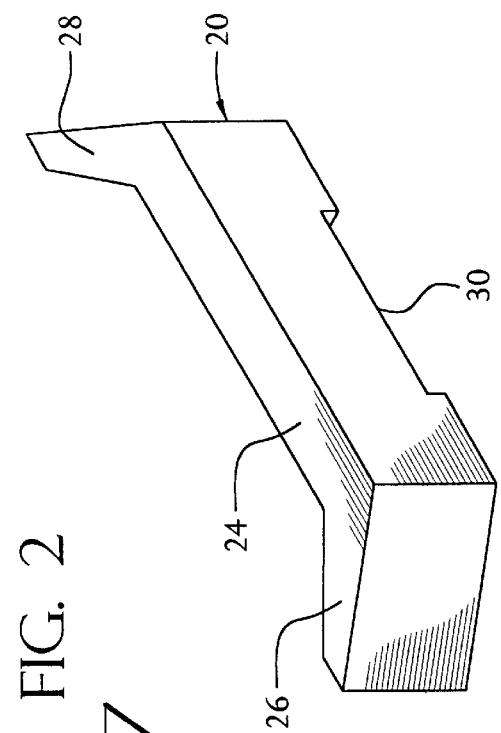
FIG. 4
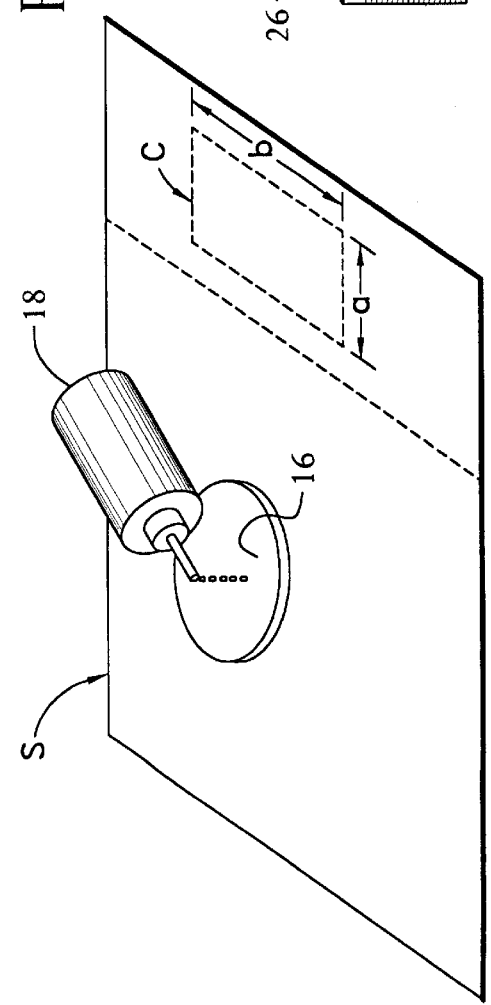
FIG. 3

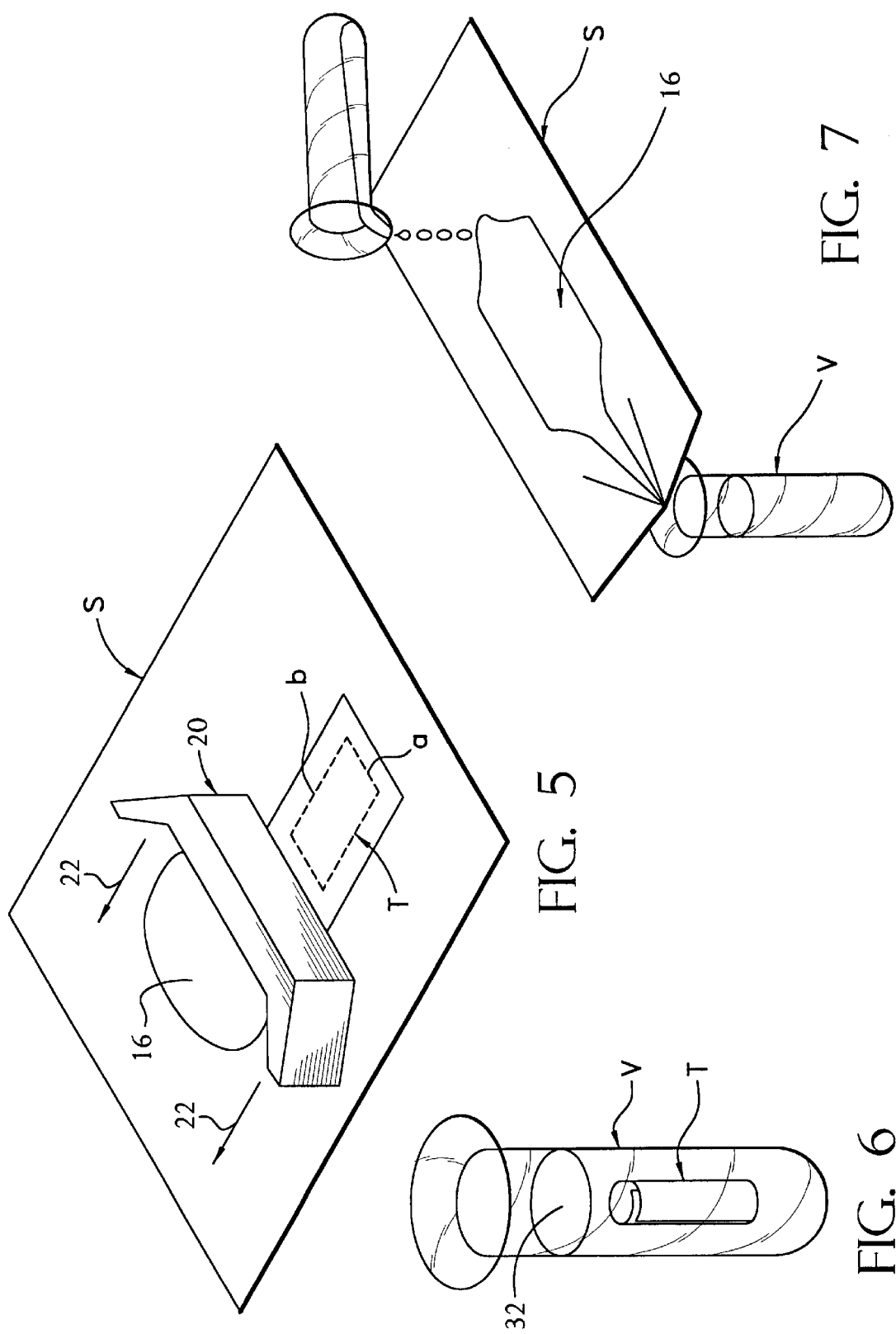

SYSTEM FOR TESTING PROPERTIES OF MATERIALS

FIELD OF THE INVENTION

The present invention relates in general to methods and apparatus for measuring certain physical properties of materials and more particularly, a chemical marker based system for determining such properties.

BACKGROUND OF THE INVENTION

Accurately determining certain physical properties of materials in a cost-effective, simple and reliable manner is an ongoing need in virtually all manufacturing industries. Precise knowledge of a material's properties enables a manufacturer to judiciously select and employ the appropriate material for an intended use or application. A specific example of an industrial practice wherein identifying suitable materials remains a somewhat crude and imprecise exercise is the selection of release papers for use with adhesive substances and products.

Release paper is used to store and protect tape, labels, stickers and other adhesives, because release paper can be removed prior to application of the adhesive to be the desired object or surface. Release paper permits the storage of pressure sensitive adhesive tape, labels and the like, while generally preserving the adhesive's tackiness. Release papers are typically coated with a thin layer of silicon or other low surface energy material in order to minimize the bond between the release paper and the adhesive.

The surface energy of release paper is very important in the tape, label and sticker industry. The surface energy of the release paper is directly proportional to the amount of adhesive substance that will remain on the release paper upon separation of the release paper and adhesive. Conversely, the degree of release of the paper is inversely proportional to its surface energy.

In the adhesives industry, it is often desirable to precisely determine how easy it is to peel off the release paper from the adhesive. The precise determination of tackiness is needed in order to determine potential uses in the industry. Currently, the degree of release is determined by commercially available mechanical testing instruments which measure the force required to peel a sample of release paper from an adhesive. Among the problems with these instruments are that they are expensive, cumbersome, imprecise and cannot be used in on-line quality control.

Sheet materials have long been tested for certain properties, such as printability and absorbency. The testing methods and apparatus for such materials have generally centered on the printing industry. Common methods and apparatus for testing the absorbency, printability or porosity of paper are taught, for example, in U.S. Pat. Nos. 4,259,862, 4,803,872, 4,911,003, 4,976,138 and 5,065,620. These patents do not disclose methods or means for testing the surface energy or releasability of the materials.

U.S. Pat. Nos. 4,541,273 and 5,141,767 describe measurement of tackiness and irregularities of surfaces, including paper, through mechanical processes employing solid and powdered marker substances. Methods and apparatus for testing absorbency and other properties of materials are taught in U.S. Pat. Nos. 2,353,852, 2,868,062, 3,559,475, 3,731,529 and 5,325,713. These involve complicated visual, photoelectrical, electrical, gravitational and ultrasonic testing methods and means.

Still other industries, particularly high technology manufacturing industries, have a need for precise and reliable on-line methods by which to determine certain properties of materials and tools used therein. The information provided by such methods would provide the interested manufacturer with information necessary to optimize tool service life, product quality and manufacturing efficiency.

An advantage exists, therefore, for a chemical testing system including method and apparatus for inexpensively, conveniently and precisely measuring properties of materials including, but not limited to, certain surface properties of substantially planar sheet materials and materials configured as regularly or irregularly surfaced three dimensional objects. Another advantage exists for such a method and apparatus that can be used in on-line quality control.

Other details, objects and advantages of the present invention will become apparent as the following description of the presently preferred embodiments of methods and apparatus of practicing the invention proceeds.

SUMMARY OF THE INVENTION

For the foregoing reasons, there is a need for a nonmechanical, economical method and apparatus to precisely measure at least one selected property of a material, particularly for use in on-line quality control.

Accordingly, the present invention provides a system including methods and apparatus for measuring at least one property of a material. The system involves applying a known amount of a chemical marker containing liquid to a defined area of the material, removing excess chemical marker liquid from the material, and determining the desired property from the quantity of chemical marker liquid either retained or not retained by the material.

The present invention also proposes employment of the presently disclosed system to establish standards wherein certain properties of materials may be quantitatively and/or qualitatively evaluated for acceptability for intended uses.

BRIEF DESCRIPTION OF THE DRAWINGS

The invention will become more readily apparent from the following description of preferred embodiments thereof shown, by way of example only, in the accompanying drawings wherein:

FIG. 1 is an enlarged elevational cross-section view of a sheet material suitable for testing by the methods and apparatus of the present invention;

FIG. 2 is a perspective view of a sheet material and adhesive label with a portion of the label being lifted from the sheet material;

FIG. 3 is a perspective view illustrating a chemical marker liquid according to the present invention being applied to a fixed area of a sheet-like material as well as a control portion of the material that is preferably removed before the chemical marker liquid is applied;

FIG. 4 is a perspective view of a nonabsorbent instrument according to the present invention for removing excess chemical marker liquid which has been previously applied to and not retained by a material to be tested in accordance with the invention;

FIG. 5 is a perspective view of the nonabsorbent instrument of FIG. 4 being drawn along a test sample of a defined area of a material to which a chemical marker containing test liquid according to the present invention has previously been applied;

FIG. 6 is a perspective view of a sample of the material of FIG. 5 immersed in a vial of washing liquid following striking of the surface of the material by a suitable nonabsorbent striking instrument such as that shown in FIG. 4;

FIG. 7 is a perspective view of a sample of a material to which chemical marker containing liquid has been previously applied and stricken by a nonabsorbent striking instrument and wherein washing liquid is being poured over the sample and collected in a vial for determination of a desired property of the material, according to a further preferred embodiment of the present invention.

DETAILED DESCRIPTION OF THE PREFERRED EMBODIMENTS

Figure 8:
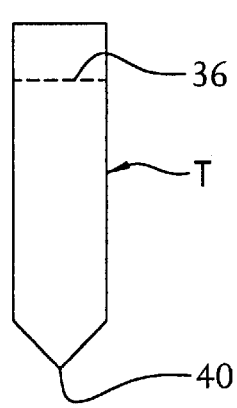
FIG. 8 is a test sample configured according to a further preferred embodiment of the present invention.

The present invention provides a simple, easy-to-use and inexpensive system whereby at least one physical property of a material, e.g., surface tension, surface energy, porosity, permeability, absorption, adsorption, printability and the like, may be determined with speed and accuracy. The system includes methods and apparatus involving deployment of at least one chemical marker substance as a qualitative and/or quantitative indicator of the desired property or properties. The invention also contemplates the establishment of empirical standards, through implementation of the presently disclosed system, against which properties of materials tested according to the invention may be qualitatively and/or quantitatively evaluated.

The system of the present invention may be used to detect at least one desired property of any substantially planar and rigid, semi-rigid, or flexible material, which material is identified by reference designation S in FIGS. 1 and 2. Material S may be fabricated from natural constituents, synthetic constituents or a combination of natural and synthetic substances. By way of illustration, material S may be a flexible sheet material, for example, a release paper. Release paper typically comprises a base layer 10 of paper or plastic and a coating 12, generally comprising silicone or some other low surface energy material adapted to promote ready separation of the release paper from an adhesive label, tape or sticker, or vice versa. When material S is a release paper, the system of the present invention may advantageously be used to measure the surface energy of the release paper, which is related to the peeling force F (FIG. 2) required to remove an adhesive-bearing article such as label 14 from the release paper.

Referring to FIGS. 3, 4 and 5, a presently preferred method according to the invention optionally entails identification of a portion of material S of length a and width b to be used as a control C (FIG. 3). The control C is thereafter preferably cut from the material S and later compared with the treated test sample T in FIG. 5.

The measurement system according to the present invention desirably utilizes a test liquid having a predetermined concentration of at least one chemical marker substance. As shown in FIG. 3, the test liquid, identified by reference numeral 16, may be dispensed manually, semi-automatically or fully automatically from any suitable applicating means 18. Although the test liquid 16 may comprise any carrier, base or vehicle liquid and marker substance combination capable of achieving the desired objects of the present invention, it is preferred that both the carrier liquid and marker substance be non-toxic. Also, the test liquid may be a mixture wherein the chemical marker substance is dissolved or suspended in the carrier liquid.

In the event material S is a release paper, for example, a suitable test liquid composition for determining the surface energy or degree of release may include 10 g of TWEEN® 20 (polyoxyethelene (20) sorbitan monolaurate), 13 g of glucose, 11 g of isopropyl alcohol, and 31 g of distilled water as a carrier or vehicle liquid. TWEEN® 20 and isopropyl alcohol function well as marker substances whose presence or absence is measured to determine the desired property (i.e., surface energy) of the release paper being tested. In research and development culminating in the present invention, it has been discovered that TWEEN® 20 and isopropyl alcohol are useful as marker substances for release papers in that they are adsorptive to the surface of such low surface energy materials. More particularly, TWEEN® 20 and isopropyl alcohol have different relative adsorptivities with respect to low surface energy materials. These differing adsorptivity characteristics are responsive to and enable differentiation between different portions, segments or ranges of surface energies within the overall scope of surface energy expected to be encountered in typical release papers and similar low surface energy materials. Hence, as a combination of marker substances, TWEEN® 20 and isopropyl alcohol are especially effective for providing resolution sufficient to accurately and reliably detect and calibrate the surface energy of release papers and similar low surface energy materials.

Glucose, an optional ingredient, functions as a convenient visual indicator for reflecting the quantity of the marker substance(s) retained or not retained by the release paper when used in conjunction with a conventional glucose meter in the manner described below. The test liquid formulation may also include, as desired or necessary, colorants, stabilizers and preservatives and any other additives necessary to enhance the performance of the test liquid.

Whereas TWEEN® 20 and isopropyl alcohol may serve well as marker substances for determining the degree of release of low surface energy material such as release paper, it will be understood that use of these ingredients is merely exemplary of but one practical application and composition of test liquid 16. That is, depending on the type of material being tested and the property of the material (e.g., permeability, porosity, printability, surface tension, and the like) that is targeted for detection and quantification, the test liquid 16 may be formulated with other marker substance(s). Likewise, under certain circumstances, the test liquid 16 may require only one or more than two marker substances to accurately gauge the target material property or properties. And, the viscosity of the test liquid 16 is preferably selected to best suit the material and property or properties to be tested.

In all of its manifestations, the present method involves applying a known quantity of the test liquid 16 to a surface of a target material. For example, a test sample of material, identified by reference character T in FIG. 5, may have a length "a" and a width "b". Following application, the test liquid is permitted to remain undisturbed on the material S for a predetermined period of time, e.g., from a few seconds up to one or more minutes. The residence time of the test liquid 16 upon material S may be influenced, inter alia, by the characteristics of the test liquid 16, the material being tested, the property or properties of the material being tested, as well as ambient temperature, humidity and related conditions.

According to a first presently preferred method of practicing the invention, a nonabsorbent striking means 20 is used to remove the excess test liquid 16 that has been applied to but not adsorbed by material S. The striking means 20 is preferably constructed as a squeegee-like instrument. As shown in FIG. 5, striking means 20 is drawn in the direction of arrows 22 across the surface of material S to strike excess test liquid from the material.

As shown in FIG. 4, striking means 20 preferably is constructed as an elongated member having a central portion 24 bounded by a pair of opposed end portions 26, 28. In operation, striking means 20 is positioned in the manner shown in FIG. 5 such that the end portions 26, 28 contain the pool of excess test liquid 16. When testing certain properties such as surface energy of especially nonadsorbent materials, e.g., release papers, the central portion 24 of striking means 20 is preferably provided with a low-profile recess 30 in its bottom surface. Recess 30 may be less than 1 mm and up to about 3 mm in height. Recess 30 prevents all of the test liquid 16 from being removed from the surface of material S and operates to produce a thin layer of test liquid over test area T of material S, thereby increasing the accuracy of the test procedure.

According to a first method, once stricken by striking means 20, the test sample T is cut and removed from material S and is then completely immersed in a known quantity of washing liquid 32 contained in vial V as shown in FIG. 6. The washing liquid may comprise any substance which promotes release of the test liquid marker constituent from the test sample T. In the instant example, the washing liquid 32 may be distilled water, optionally including surfactant(s) or other constituents to enhance release of the marker substance(s). For instance, a suitable washing liquid may comprise 0.5 g Triton® X-100 (t-octylphenoxypolyethoxyethanol) and 0.25 g of disodium EDTA dehydrates dissolved in 50 ml of distilled water. The pH of the washing liquid may be adjusted to substantially neutral by the addition of suitable basic materials.

It is also desirable to cover and shake the vial of washing liquid for a period of time sufficient to substantially completely release the chemical marker substance into the washing liquid. Following this, the washing liquid containing the chemical marker substance may be tested using a conventional visual or other testing system. In this regard, any commercially available chemical detection system suitable for detecting the optional visual indicator, e.g., glucose, corresponding in quantity to the chosen chemical marker substance may be used to detect the chemical marker substance concentration in the washing liquid. An example of a commercially available indicator detection system includes, without limitation, the ONE-TOUCH® BASIC glucose detection system manufactured by Lifescan of Milpitas, Calif. (not illustrated), which includes a hand-held meter and test strip.

A small quantity such as one or a few drops of the washing solution is extracted from the vial V using a dropper or the like and then is deposited onto the test strip. The test strip then typically changes color and is measured by the meter to determine the glucose concentration in the vial. This concentration corresponds to the amount of chemical marker substance retained or adsorbed by the material, which, for release papers and the like, is an indication of surface energy and degree of release. Indeed, the observed chemical marker concentration may be further compared to an empirically generated data base, table, graph or chart specifically created for the material and property or properties to be tested, as is described more fully in connection with FIG. 14. Such comparison may be used to readily convert the measured property information into a quantified alphanumeric, symbolic or other convenient designation which will quickly enable the operator to determine whether the material S meets its intended property specifications.

Referring to FIG. 7, a further embodiment of the method of the present invention involves pouring a known quantity of a suitable washing liquid over the material S following application and striking of the test liquid 16 in the manner described in connection with FIG. 5. The washing liquid removes the excess test liquid that is not adsorbed by the material S. The washing liquid is collected in vial V and a small quantity of the washing liquid is tested as described above. The chemical marker concentration in the washing liquid according to this embodiment represents the amount of marker substance not adsorbed into the material S, which can be interpreted directly as, or converted into, meaningful information reflecting the magnitude of the desired property or properties of the material being tested.

According to another embodiment of the present invention illustrated in FIGS. 8, 9, 10 and 11, an absorbent instrument 34 may be used to collect the test liquid 16 adsorbed by material test sample T. The absorbent instrument 34, which may be, for example, a simple swab or sponge-like device, absorbs test liquid from the test sample T.

According to this embodiment, silicon tape or other sealant is applied to a surface of the material which is not to be tested. Thereafter, a 1 cm wide and 4 cm long strip is cut from the material to form test sample T. The test sample T is preferably marked as indicated by dashed line 36 at a distance of at least about 0.5 cm from the top of the strip to permit the manual gripping of the strip by the user's fingers or with tweezers, forceps or the like.

Figure 9:
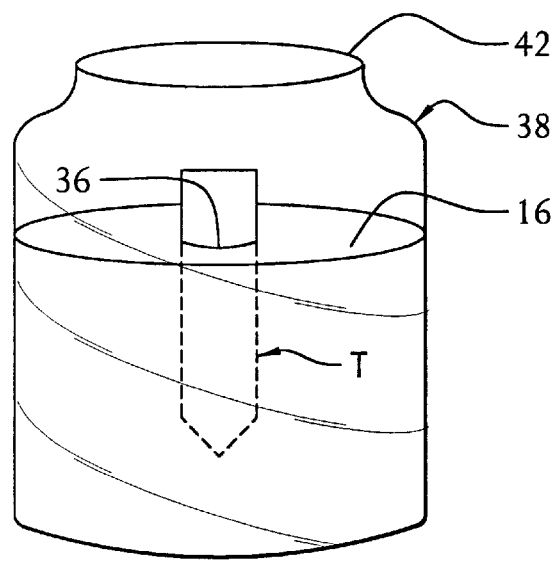
FIG. 9 is a perspective view of the test sample of FIG. 8 immersed in a quantity of test liquid.

As depicted in FIG. 9, test sample T is then immersed to mark 36 in test liquid 16 contained in a jar, beaker or similar receptacle 38 for about 15 seconds. The test sample is then removed from the test liquid 16 and excess test liquid is permitted to drain back into receptacle 38. To promote drainage of the test sample, the lower edge thereof is preferably cut into an angled tip 40 (FIG. 8) which may be held against the mouth 42 of receptacle 38 for approximately 10 seconds to promote flow between tip 40 and receptacle 38.

Figure 10:
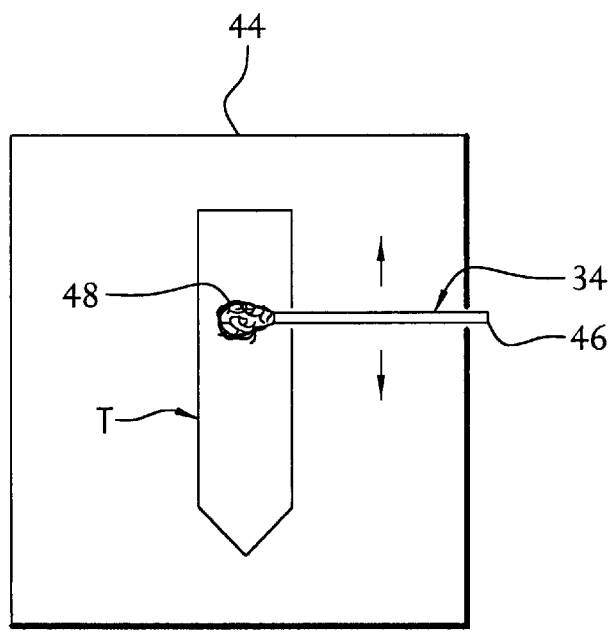
FIG. 10 is a plan view of the test sample of FIGS. 8 and 9 being contacted by an absorbent means following immersion of the test sample in a test liquid.

As shown in FIG. 10, the test sample T is laid, sealant side down, on an absorbent 44 such as a sheet of absorbent paper or the like which absorbs residual test liquid 16 that may be present on the downwardly facing side of the test sample T. After several seconds, the user then grasps a handle 46 of the absorbent instrument 34 and brushes the absorbent tip 48 thereof over the entire exposed surface of the test sample T until essentially all available residual test liquid 16 is absorbed into tip 48.

Figure 11:
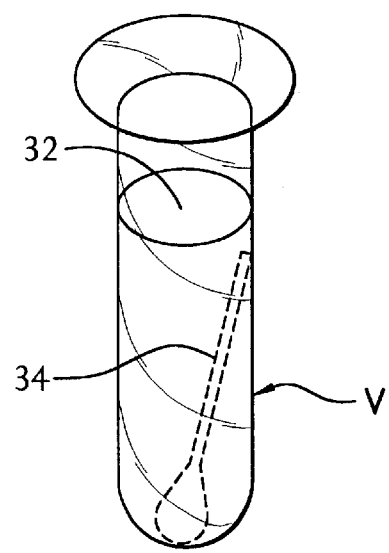
FIG. 11 is a perspective of the absorbent means of FIG. 10 immersed in a vial of washing liquid following contact of the absorbent means with the test sample.

Thereafter, as shown in FIG. 11, the absorbent instrument 34 is then completely immersed in a known quantity of washing liquid 32 in vial V. The vial is preferably vigorously shaken for about 30 seconds to essentially completely release the chemical marker substance from the absorbent instrument into the washing liquid. A small quantity, e.g., about 15 µl, of marker substance containing washing liquid, which, if it includes a suitable visual indicator substance, may be applied to the test strip of an appropriate visual indicator detection system. The wetted test strip is measured by the detection system's test meter to detect the indicator concentration and, correspondingly, the chemical marker substance concentration in the washing liquid. According to this embodiment, the chemical marker concentration corresponds to the amount of test liquid retained or adsorbed by the material. This data, in turn, may be used to determine the desired property thereof, e.g., the surface energy and concomitant degree of release of a release paper.

Figure 12:
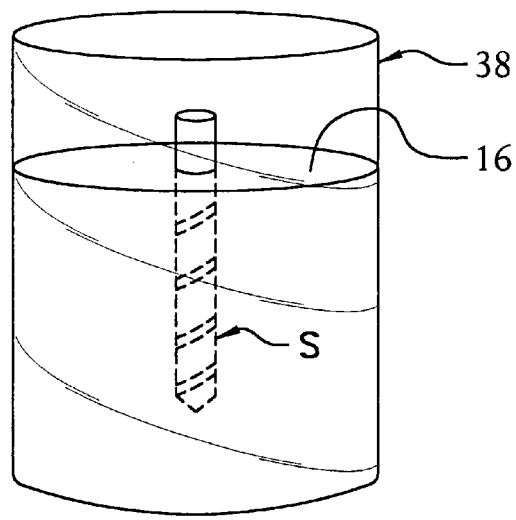
FIGS. 12 and 13 are sequential views of a method according to the present invention for determining a property of an irregularly shaped three-dimensional object.
Figure 13:
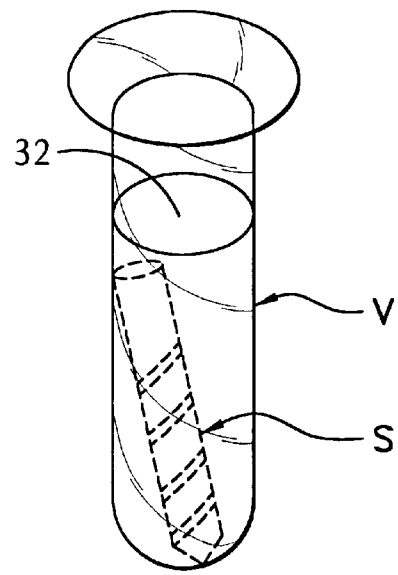

FIGS. 12 and 13 illustrate an embodiment of the invention wherein the material S whose selected property or properties are to be determined is configured, in contrast with the substantially planar sheet materials discussed in the previous embodiments, as a three dimensional object. The three dimensional object may have a regular or irregular surface. For purpose of illustration, but not of limitation, material S may be embodied as machine tool such as a saw blade or, as shown, a drill bit.

Certain high technology industries require that the tools used therein and the products manufactured thereby be maintained within tight tolerances and specifications. For instance, certain saw blades, drill bits and the like may be coated with hardened and/or friction reducing materials. As the tool is used, such coatings become worn. As the wear proceeds, the tools may not efficiently penetrate the products they are designed to machine. Consequently, the worn tools may, in fact, damage the products by virtue of poor cut quality, undue abrasion, excessive friction heat, and the like. Under such circumstances, the damaged products may have to be discarded, thereby needlessly reducing efficiency and throughput capacity of the manufacturing operation.

The system according to the present invention as depicted in FIGS. 12 and 13 allows a user to easily determine, in a simple and rapid on-line quality control process, whether a particular material S is or is not within its intended operational specifications. More particularly, a user may simply remove material S (e.g., a drill bit) from its drive machinery and immerse it in a chemical marker substance containing test liquid 16 in receptacle 38 for a predetermined period of time. The user then withdraws the material S from the test liquid 16 and allows excess test liquid to drain back into the receptacle 38. Following this, the object being tested may be immersed in washing liquid 32 contained in vial V. It will be appreciated that the test liquid 16 and washing liquid 32 will have compositions selected for optimum determination of the target property or properties under scrutiny. The vial V may then be shaken to promote release of the test liquid from the material S.

Similar to the embodiment of the invention described hereinabove in connection with FIG. 6, a small quantity of washing solution 32 may then be extracted from vial V and deposited onto a suitable test strip. The wetted test strip is then measured by a suitable testing meter to determine the chemical marker substance concentration in the vial. This concentration may correspond to the amount of chemical marker substance retained or adsorbed by material S which, for machine tools such as drill bits, saw blades and the like, may be an indication of the hardness, slickness or other characteristic of the material.

If the material S is determined to be within design specifications, it may be quickly returned to service and periodically re-evaluated. Conversely, if material S is not within specifications it may be quickly replaced. The method reflected in FIGS. 12 and 13 finds particularly beneficial application in testing new, used and refurbished three-dimensional dimensional materials S configured as machine tools or the like but is not limited to such uses.

Although described specifically in connection with chemical marker detection systems employing calorimetric detection schemes, the invention is not so limited. That is, it is also contemplated that detection of the chemical marker concentration retained or not retained by the material sample may be accurately determined by any suitable mechanism including, without limitation, gravimetric, radiological, refractive, spectroscopic, fluorescent, and related detection means and processes. Moreover, any and all steps of any of the disclosed embodiments of the present invention may be performed manually, automatically or a combination thereof.

Figure 14:
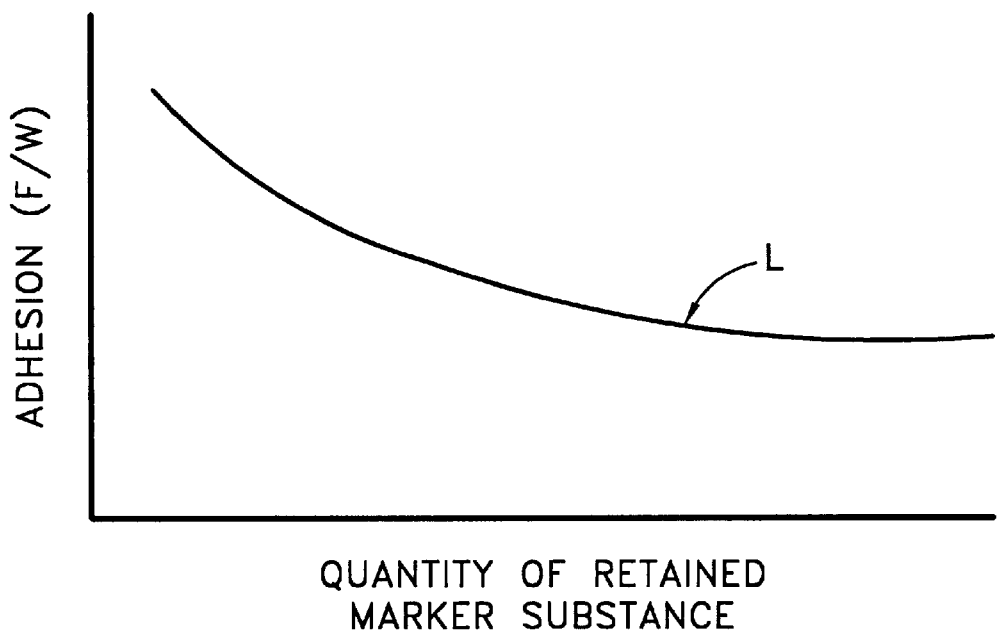
FIG. 14 is an example of a standard empirical graph of adhesion, expressed in terms of peeling force divided by width of a material sample versus the amount of test liquid retained by the material sample, which can be generated through implementation of the present invention and against which a material of unknown adhesion characteristics, tested according to the present invention, may be evaluated.

FIG. 14 is an exemplary graph or curve which may be empirically generated via repeated implementation of the methods disclosed herein in order to establish a standard against which a property or properties of a selected material, also tested according to the present invention, may be qualitatively and/or quantitatively evaluated. Although standard curves may be generated for any of the aforementioned materials and properties thereof, FIG. 12 represents a non-limitative example of such a standard curve wherein the adhesion or surface energy characteristics of a material sample (as expressed in terms of the peeling force F divided by the width W of the sample) may be determined as a function of the amount of chemical marker substance retained by a specific sample of known width. Once the quantity of the retained marker substance is measured (according to any of the methods described above) that value is compared against the acceptable standard threshold line L for a sample of the width. If the adhesion is determined to be above (or below) line L, the sample may then be easily determined to have acceptable or unacceptable adhesion characteristics. Other preferred embodiments of standard curves or graphs which may be generated and utilized in accordance with the present invention include, without limitation, curves of absorption, adsorption, surface energy, surface tension, permeability, printability and porosity vs. the chemical marker substance retained or not retained by a test sample T of a given material S. Alternatively, the empirically generated test data may be expressed in tabular form as represented, for example, in Table 1.

TABLE 1

| DETECTED GLUCOSE CONCENTRATION (mg/deciliter - - two measurements) | RELEASE SCALE (Newtons/100 mm width) |
|---|---|
| 20, 21 | 13–27 |
| 39, 40 | 63–87 |
| 47, 48 | 118–152 |

A sample of release paper may then be tested according to any of the methods herein described to obtain the marker substance concentration in the relevant washing liquid and this result may be compared against empirical tabular data such as illustratively, but not limitatively, set forth in Table 1.

The invention has been described in detail above for the purpose of illustration. Such detail is only for that purpose and it is to be understood that variations can be made therein without departing from the spirit and scope of the invention except as it may be limited by the claims.

What is claimed is:

1. A method for measuring at least one property of a material, said method comprising the steps of:

applying a test liquid to said material, said test liquid containing a predetermined quantity of a first chemical marker substance for determining a portion of said at least one property and at least one additional chemical marker substance for determining another portion of said at least one property;

removing the portion of said test liquid from said material that is not retained by said material; and determining said at least one property from the amount of said chemical marker substance present in said test liquid which is either retained or not retained by said material.

2. The method of claim 1 wherein said material is a natural, synthetic or combined natural and synthetic sheet material.

3. The method of claim 1 wherein said removing step comprises striking said material with a nonabsorbent instrument.

4. The method of claim 1 wherein said determining step comprises determining said at least one property by one of visual, colorimetric, gravimetric, refractive, spectroscopic, fluorescent and radiological testing.

5. An apparatus for measuring at least one property of a material, said apparatus comprising:

means for applying a test liquid to said material, said test liquid containing a predetermined quantity of a first chemical marker substance for determining a portion of said at least one property and at least one additional chemical marker substance for determining another portion of said at least one property;

means for removing the portion of said test liquid from said material that is not retained by said material; and means for determining said at least one property from the amount of said chemical marker substance present in said test liquid which is either retained or not retained by said material.

6. The apparatus of claim 5 wherein said material is a natural, synthetic or combined natural and synthetic sheet material.

7. The apparatus of claim 5 wherein said removing means comprises a nonabsorbent instrument for striking said material.

8. The apparatus of claim 5 wherein said determining means comprises means for determining said at least one property by one of visual, calorimetric, gravimetric, refractive, spectroscopic, fluorescent and radiological testing.

9. The method of claim 1 wherein said material is a three dimensional object.

10. The method of claim 1 wherein said removing step comprises washing said material with a washing liquid, said washing liquid carrying away said test liquid not retained by said material.

11. The method of claim 1 wherein said removing step comprises absorbing said test liquid retained by said material with an absorbent instrument.

12. The method of claim 5 wherein said material is a three dimensional object.

13. The apparatus of claim 5 wherein said removing means comprises means for washing said material with a washing liquid, said washing liquid carrying away said test liquid not retained by said material.

14. The apparatus of claim 5 wherein said removing means comprises means for absorbing test liquid retained by said material.

15. The method of claim 9 wherein said three dimensional object has an irregular surface.

16. The method of claim 10 wherein said washing liquid comprises distilled water.

17. The method of claim 10 wherein said determining step comprises testing said washing liquid, said washing liquid including said chemical marker substance of said test liquid not retained by said material.

18. The method in claim 11 wherein said determining step comprises detecting the amount of said chemical marker substance absorbed by said instrument.

19. The method of claim 12 wherein said three dimensional object has an irregular surface.

20. The apparatus in claim 13 wherein said washing liquid comprises distilled water.

21. The apparatus in claim 13 wherein said determining means comprises means for detecting the amount of said chemical marker substance contained in said washing liquid following washing of said material.

22. The apparatus in claim 14 wherein said determining means comprises means for detecting the amount of said chemical marker substance absorbed by said absorbing means following absorption of said test liquid retained by said material.

* * * * *